(12) United States Patent
Mosseri (10) Patent No.: US 6,482,237 B2
(45) Date of Patent: Nov. 19, 2002

(54) TOTAL HIP PROSTHESIS ADAPTED TO BE IMPLANTED ENDO-ARTICULARLY AND ITS AUXILIARY DEVICE AND METHOD OF IMPLANTATION

(76) Inventor: Raphael Mosseri, 38 Rue-Beaujon, 75008 Paris (FR)

( * ) Notice: Subject to any disclaimer, the term of this patent is extended or adjusted under 35 U.S.C. 154(b) by 35 days.

(21) Appl. No.: 09/779,668

(22) Filed: Feb. 9, 2001

(65) Prior Publication Data

US 2001/0012967 A1 Aug. 9, 2001

Related U.S. Application Data

(62) Division of application No. 09/202,415, filed as application No. PCT/FR97/01080 on Jun. 13, 1997, now Pat. No. 6,231,611.

(30) Foreign Application Priority Data

Jun. 14, 1996 (FR) ............................................. 96 07452

(51) Int. Cl.[7] ................................................ A61F 2/32
(52) U.S. Cl. ............................. 623/22.12; 623/22.15; 623/23.11
(58) Field of Search .................... 623/22.12, 22.11, 623/22.4, 23.12, 23.39, 902, 22.15, 22.25, 23.11; 128/898

(56) References Cited

U.S. PATENT DOCUMENTS

| | | |
|---|---|---|
| 2,668,531 A | 2/1954 | Haboush |
| 2,785,673 A | 3/1957 | Anderson |
| 4,123,806 A | 11/1978 | Amstutz et al. |
| 4,173,797 A | 11/1979 | Langlais et al. |
| 4,274,164 A | 6/1981 | Rehder et al. |
| 4,475,549 A | 10/1984 | Oh |
| 4,672,957 A | 6/1987 | Hourahane |
| 4,976,740 A | 12/1990 | Kleiner |
| 5,127,920 A | 7/1992 | MacArthur |
| 5,163,940 A | 11/1992 | Bourque |
| 5,192,327 A | 3/1993 | Brantigan |
| 5,376,092 A | 12/1994 | Hein et al. |
| 5,385,567 A | 1/1995 | Goble |
| 5,429,641 A | 7/1995 | Gotfried |
| 5,474,560 A | 12/1995 | Rohr, Jr. |
| 5,649,930 A | 7/1997 | Kertzner |
| 5,725,593 A | 3/1998 | Caracciolo |
| 5,814,050 A * | 9/1998 | Benson ........................ 606/102 |

FOREIGN PATENT DOCUMENTS

| | | |
|---|---|---|
| DE | 2808740 | 9/1979 |
| DE | 3538346 A1 | 5/1987 |
| DE | 3923154 A1 | 1/1991 |
| DE | G9402828.1 | 7/1994 |
| EP | 0028546 A1 | 5/1981 |
| FR | 1538101 | 8/1968 |
| FR | 2395739 | 1/1979 |
| FR | 2406433 | 5/1979 |
| FR | 2519545 | 7/1983 |
| FR | 2578739 | 9/1986 |
| FR | 2653326 | 4/1991 |
| GB | 1467332 | 3/1977 |
| WO | WO 9107932 | 6/1991 |
| WO | WO 9515133 | 6/1995 |

* cited by examiner

Primary Examiner—Eduardo C. Robert
(74) Attorney, Agent, or Firm—Young & Thompson

(57) ABSTRACT

A total hip prosthesis comprises a cotyloid implant consisting of a metal cup to be anchored in the acetabulum, a polyethylene insert which provides an intermediate implant inserted into the cavity of the cup, and a femoral implant consisting of a cap having an outer convex surface which is slidably postionable within the insert cavity. An inner concave surface of the femoral implant is implantable on the head of the femur. The prosthesis is particularly suitable for endo-articular implantation.

9 Claims, 8 Drawing Sheets

TOTAL HIP PROSTHESIS ADAPTED TO BE IMPLANTED ENDO-ARTICULARLY AND ITS AUXILIARY DEVICE AND METHOD OF IMPLANTATION

This application is a division of application Ser. No. 09/202,415, filed on Feb. 22, 1999, now U.S. Pat. No. 6,231,611. Application Ser. No. 09/202,415 is the national phase of PCT International Application No. PCT/FR97/01080 filed on Jun. 13, 1997 under 35 U.S.C. §371. The entire contents of each of the above-identified applications are hereby incorporated by reference.

BACKGROUND OF THE INVENTION

The present invention relates to a total hip prostheses adapted to be implanted endo-articularly and its auxiliary device. Upon deterioration of the articulation of the hip, for example in the case of arthrosis or rheumatoid arthritis, it may be necessary to replace the coxo-femoral articulation by a prosthesis.

Certain prostheses now known comprise:
- a cotyloid implant constituted by a metallic cup provided with primary anchoring means in the acetabulum and having externally an overall hemispheric surface and internally a concave recess,
- an insert forming an intermediate implant generally of plastic, such as polyethylene, provided with means for connection with the cup and having externally a surface complementary to that of the recess of the cup in which it is received and internally a substantially hemispherical recess, and
- a metallic femoral implant constituted by a femoral rod implanted in the medullar channel of the femur and a prosthetic neck surmounted by a spherical femoral head which will be articulated in the recess of the insert.

Implanting such a prosthesis requires an expensive total arthroplasty technique of the hip, which is subject to a number of requirements.

Thus, it is necessary to provide an ablation of the femoral head and a portion of the femoral neck to implant the femoral rod in the midportion of the femur, even if the degeneration of the articulation hasn't reached the neck or head of the femur.

In addition to ablation of the head of the femur, it is necessary to do the same for all of the articular capsule.

On the other hand, in this open surgery, it is necessary to provide access of about ten centimeters and to dislocate the articulation to be able to introduce the various instruments for cutting and the various implants.

SUMMARY OF THE INVENTION

The present invention therefore has for its object to provide a new total hip prosthesis permitting limiting the resection to only the injured articular surfaces so as to preserve the integrity of the head of the femur and of the capsule, and to carry out minimal arthrotomy.

To this end, the invention has for its object a total hip prosthesis comprising: a cotyloid implant constituted a metallic cup provided with primary anchoring means in the acetabulum and having externally an overall convex surface and internally a generally concave recess,

- an insert forming an intermediate implant for example of a plastic such as polyethylene, provided with connection means with the cup and having externally a shape complementary to the recess of the cup in which it is received and internally a concave bearing recess, and
- a metallic femoral implant adapted to be received slidably in the bearing recess of the insert and implanted in the femoral bone, characterized in that the femoral implant is constituted by a cap having externally a convex surface adapted to come into sliding bearing engagement in the recess of the insert and internally a concave surface adapted to implant itself in the spongy bone of the femoral head.

According to another characteristic of the invention, the femoral implant comprises a small screw-threaded rod which projects perpendicularly to the center of its concave surface and a separate element forming a screw-threaded nut internally for screwing on said screw-threaded rod and externally screw-threaded to screw into the femoral head along the axis of the femoral neck.

Preferably, the pitch of the external screw-threading of the nut is greater than that of its internal screw-threading.

According to another characteristic of the invention, the cotyloid implant is pierced at its center for the passage of a screw-threaded lug for primary anchoring in the acetabulum.

On the convex surface of the cotyloid implant and the concave surface of the femoral implant can be provided asperities or small points to improve the anchoring respectively in the acetabulum and the femoral head.

According to still another characteristic, the mentioned connection means are snap-in means of the mortise and tenon type at the periphery of the base of the cup and of the insert.

According to another characteristic, each implant comprises at its periphery a local coupling means such as substantially radial female thread, to permit its coupling to a carrying arm.

The present invention also relates to an auxiliary device for endo-articular implantation of the prosthesis mentioned above, characterized in that it comprises:
- a plurality of instruments adapted to be introduced along the axis of the femoral neck from the region of the trochanter base toward the coxo-femoral articular space such that their free distal end serves to center and guide the prosthesis during its implantation,
- a carrying arm that can support removably at its distal end the mentioned implants or a drill for introducing them by a lateral access route in the mentioned articular space, and
- a support structure adapted to be positioned parallel to the axis of the femur and at the lower end of which is selectively ensleeved or introduced freely in rotation and/or slidably one of the mentioned instruments and at the upper end of which is ensleeved the carrying arm slidably and inclinably to engage the implant or the drill on the distal end of an instrument opening into the articular space.

The distal end of the instruments defines a point of intersection with the drills or the implants and gives the central working point in the coxo-femoral articulation.

In a particular embodiment, the distal end of the carrying arm is screw-threaded to screw into a female thread provided at the periphery of the implant or of the drill to be supported.

According to another characteristic, the device can comprise a hemispheric femoral drill whose internal surface is adapted to grind down the head of the femur, said drill being pierced at its center to receive secured in rotation therewith the distal end of an instrument which is adapted to be connected at its proximal end to a rotatable drive motor.

In this case, the device can comprise moreover a bearing arm ensleeved parallel to the carrying arm at the upper end of the support structure and constituted by a rod whose distal portion is in the form of an arc of a circle matching the shape of a meridian from the external surface of the femoral drill and of which the distal end is adapted to bear in a pivotal manner on the center of said drill.

The support structure can thus also comprise a means forming a vise whose movable jaw is constituted by the bearing arm and the fixed jaw is secured to said structure, the two jaws being adapted to be selectively brought together so as to press the femoral drill against the head of the femur.

According to another characteristic of the invention, the device can comprise a hemispheric cotyloid drill whose external surface is adapted to grind down the cotyloid cavity, said cotyloid drill being pierced at its center to receive and be secured to in rotation the distal end of an instrument which is adapted to be connected at its proximal end to a rotatable drive motor.

In this case, the device can moreover comprise an instrument forming a bit adapted to traverse the central hole of the cotyloid drill to hollow in the acetabulum bone a central cotyloid hole for reception of a screw-thread lug of the cotyloid implant.

According to still another characteristic, the distal end of the instrument has a shape complemental to the head of the screw-threaded lug mentioned above, for screwing into the centro-cotyloid hole.

In a particular embodiment, the device comprises a cotyloid impactal element temporarily secured in the recess of the insert by frangible peripheral points. The impact element can be provided with a recess of a shape complementary to the distal end of the instrument or a small screw-threaded rod which projects perpendicularly to the center of its lower surface.

The device thus comprises preferably an instrument whose distal end is internally screw-threaded in a manner complementary to the screw-threaded rod of the femoral implant and/or the impactor element.

According to still another characteristic, the device of the invention comprises an instrument whose distal end supports removably and is secured in rotation to the nut no of the femoral implant to screw this latter into the head of the femur and on the screw-threaded rod of the femoral implant.

It can be provided that in the engaged position of the drill or the implant on an instrument, this latter and the carrying arm define between them an angle of about 60°.

To this end, the support structure can have an elbowed shape whose upper and lower branches define an angle of about 120°.

BRIEF DESCRIPTION OF THE DRAWINGS

The invention will be better understood, and other objects, details, characteristics and advantages of it will become more clearly apparent in the course of the description which follows, of a particular embodiment of the invention which is at present preferred, given solely by way of illustration and not limitatively, with reference to the accompanying schematic drawings, in which.

DESCRIPTION OF THE PREFERRED EMBODIMENTS

There will now be described a particular manner of emplacing the total hip prosthesis of the invention, with reference to the accompanying drawings.

The patient to be operated on is first emplaced in dorsal decubitus on an orthopedic table with traction and abduction of 60° of the lower limb to be operated on.

It will be noted that it will not be necessary to dislocate the coxo-femoral articulation in the course of the procedure.

The surgeon introduces from the trochanter base region and along the axis of the femoral neck, a guide (not shown) which opens at the level of the coxo-femoral articulation. He then hollows out along the axis of the femoral neck with the aid of tap (not shown) guided by the pin, a cylindrical longitudinal space 22 suitable for the introduction of various auxiliary instruments of which the distal end can open at the level of the coxo-femoral articulation.

Figure 1:
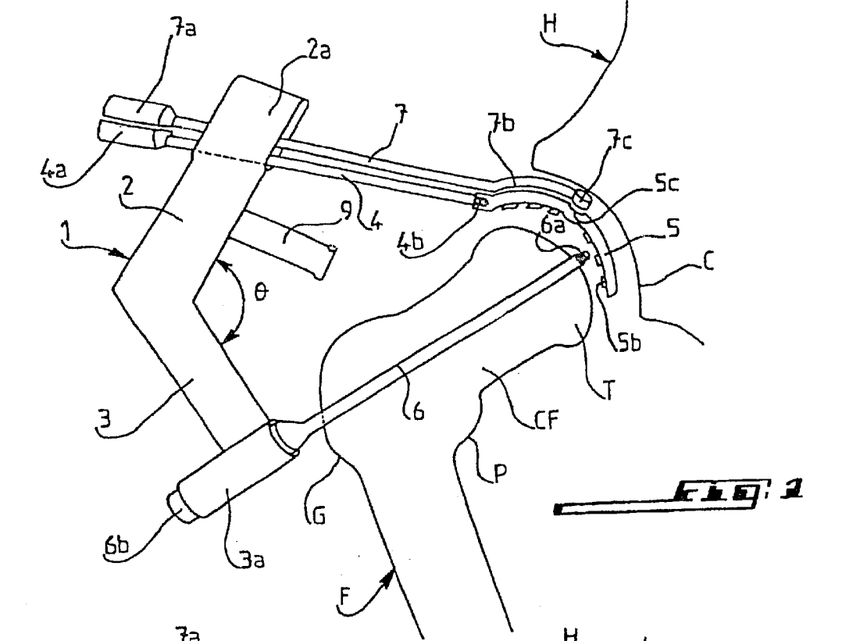
FIGS. 1 to 3 are fragmentary schematic views showing the successive steps of the resection of a cartilaginous surface of the head of the femur with the auxiliary device of the invention.

There is shown in FIG. 1, on the one hand the upper portion of the midportion of the femur F, the large trochanter G and the small trochanter P, the femoral neck CF and the femoral head T, and, on the other hand, the cotyloid cavity C of the hip H.

The auxiliary device of the invention comprises an elbowed support structure 1 whose upper and lower legs 2 and 3 define between them an angle θ of the order of 120°. The lower leg 3 comprises at its free end a cylindrical sleeve 3a, whilst the upper leg 2 comprises at its free end an oblong sleeve 2a with an axial trapezoidal cross-section.

The auxiliary device comprises a carrying arm 4 constituted by a rod whose proximal end is prolonged by handle 4a and the distal end 4b is screw-threaded.

The hemispherical femoral drill 5 comprises at its periphery a radial female thread 5a into which is screwed the screw-threaded end 4b of the carrying arm 4. The femoral drill 5 comprises on its concave surface metallic asperities 5b having a grinding effect, whilst its convex surface is smooth. The femoral drill 5 is pierced at its center with a hexagonal hole 5c into which is engaged for rotation therewith the distal end of corresponding shape 6a of a first instrument 6.

The instrument 6 is also constituted by a rod whose distal end has a hexagonal end 6a and whose proximal end is prolonged by a handle 6b which is retained by the sleeve 3a of the support structure 1.

The rod of the instrument 6 of course passes through the femoral neck CF along its axis, which also constitutes the axis of rotation of the rod.

Figure 5:
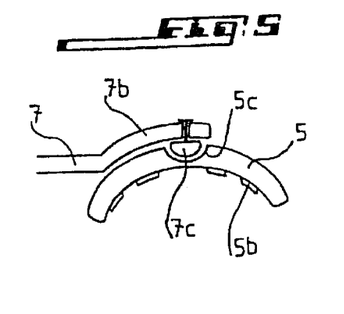

With the carrying arm 4 is associated another arm 7, a so-called bearing arm, constituted by a rod whose proximal end is also prolonged by handle 7a of a shape complementary to the handle 4a and whose distal portion is in the form of an arc of a circle 7b matching the shape of a meridian from the convex surface of the femoral drive 5, the distal end 7c of this rod being provided with a rotor (see FIG. 5). to bear pivotally on the center 5c of said drill.

The instrument 6 is first introduced along the axis of the femoral neck CF until its distal end 6a enters the coxofemoral articular space, so that instrument 6 being supported with its handle 6b by the lower leg 3 of the support structure which is positioned parallel to the axis of the femur.

With the assembly of the bearing and carrying arms 4 and 7 maintained parallel to each other, the femoral drill 5 is introduced through a small arthrotomy, for example of the order of 4 cm in the mentioned articular space, as is shown in FIG. 1.

Figure 2:
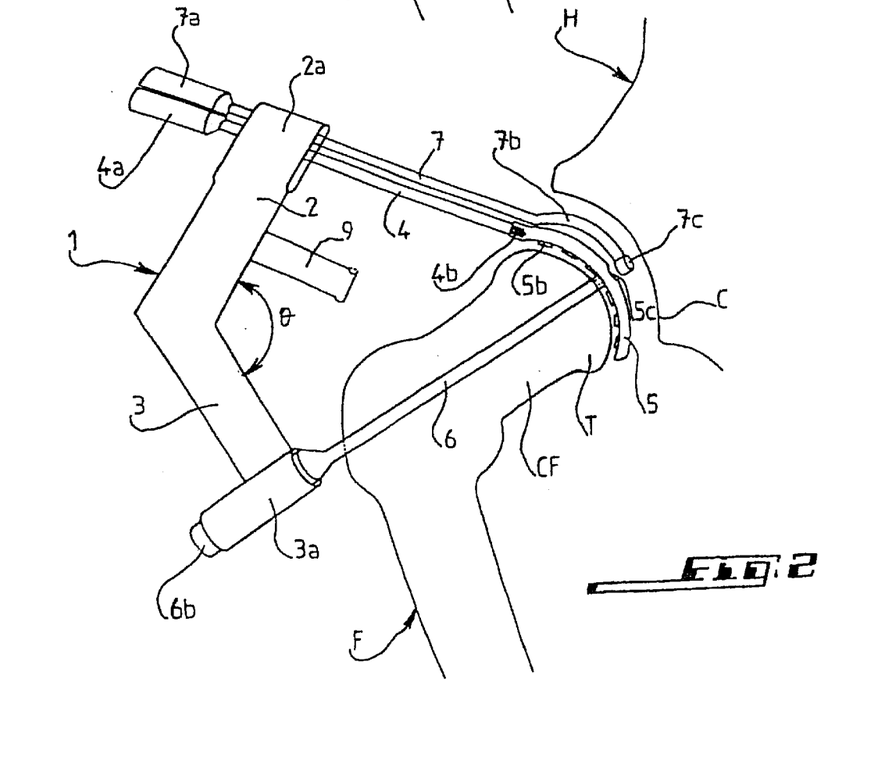

The two arms 4 and 7 which are guided by the sleeve 2a of the upper arm 2 can slide in the latter to bring the drill 5 facing the instrument 6 and to within said trapezoidal sleeve 2a to engage the central hole 5c of the drill 5 on the distal end 6a of the instrument 6, as shown in FIG. 2.

It will be seen, by comparing FIG. 1 to FIG. 2, that the arms 4 and 7 pass from one side to the other of the trapezoid of the sleeve 2a, which causes the inclination of these arms to vary. In the position shown in FIG. 2, the instrument 6 forms an angle of about 60° with the arms 4 and 7, given that in this position the instrument 6 and the arms 4 and 7 are respectively perpendicular to the lower and upper legs 3 and 2.

Figure 3:
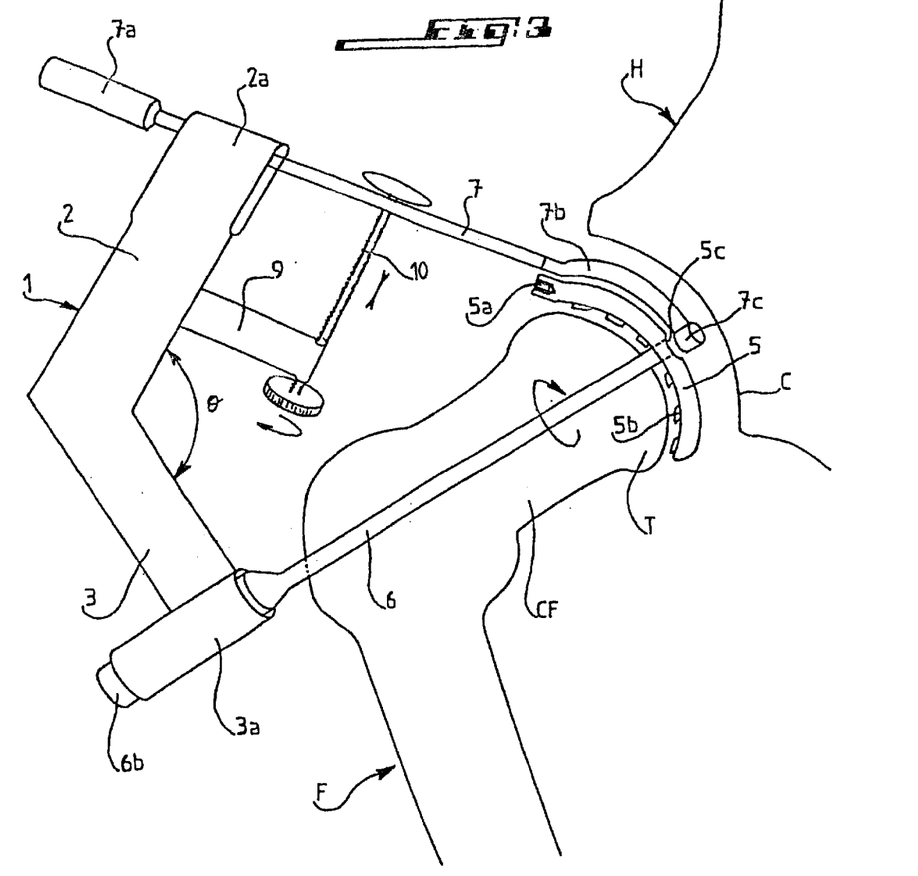

Once the drill 5 is seated on the instrument 6, the carrying arm 4 is retracted which would otherwise prevent rotation of the drill 5 (see FIG. 3).

Figure 4:
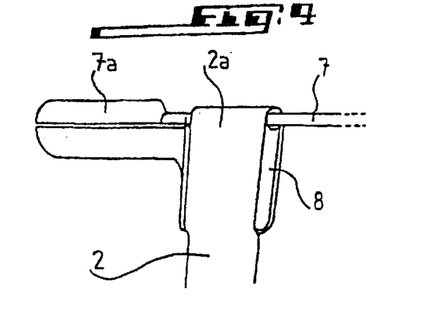
FIGS. 4 and 5 are detailed views respectively of the proximal end and of the distal end of the bearing arm shown in FIG. 3.

On the other hand, the bearing arm 7 is maintained in position at its distal end 7c against the drill 5 and at its proximal portion by a temporary semi-rigid or resilient block 8 (shown in FIG. 4) which fills the empty space within the sleeve 2a.

To apply the drill 5 against the cartilaginous surface of the femoral head T, there is used a member functioning as a vise to press the arm 7 against the drill 5.

This member forming a vise is constituted by an arm 9 perpendicularly fixed to the upper leg 2 to serve as a fixed jaw and a knurled set screw 10 to bring the bearing arm 7 in, which serves as the movable jaw relative to the fixed jaw.

When the drill 5 is in bearing relationship against the femoral head T, the instrument 6 can then be driven in rotation by a motor (not shown) connected to its handle 6b, which gives rise to conjoint rotation of the drill 5.

Once the drilling of the femoral head T is completed, the surgeon no longer needs to use the bearing arm 7 and the member forming a vise.

Extraction of the femoral drill 5 from the articular cavity is carried out by means of a gripping pliers.

For the resection of the cotyloid cavity C, there is used a cotyloid hemispherical drill 11 whose convex surface is provided with metallic projections 11b having a scraping action whose concave surface is smooth. This cotyloid drill 11 comprises also a radial peripheral internal screw-threading 11a in which can be screwed the distal end 4b of the carrier arm 4. This latter permits engaging the cotyloid drill 11 on the distal end 4a of another instrument in the form of a bit 12 (see FIG. 6).

The bit 12 has a conical point at its distal end 12a which is prolonged by a handle 12b at its proximal end to be able to be ensleeved in the sleeve 3a. It will be seen that the handle 12b is connected to a rotary drive rotor 13, shown partially and schematically in FIG. 6.

Figure 6:
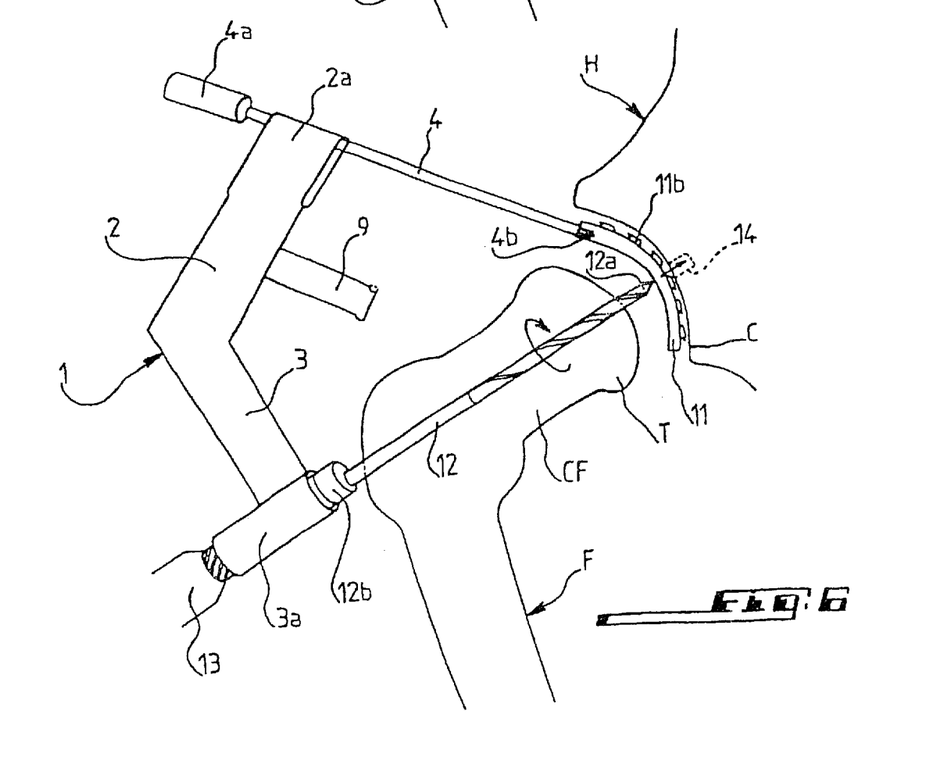
FIGS. 6 to 8 are views analogous to FIG. 1, which show the successive steps of the resection of the acetabulum.

The bit 12 permits hollowing a centro-cotyloid hole 14 in the bottom of the acetabulum C for reasons indicated hereinafter.

Figure 7:
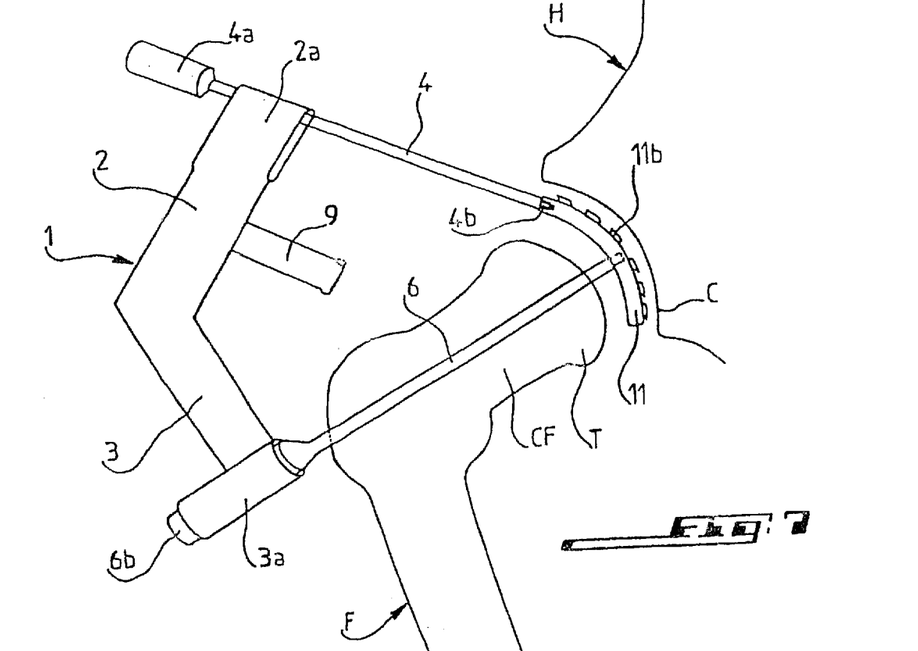

When the centro-cotyloid hole 14 has been hollowed out, the bit 12 is withdrawn from the support structure 1 and replaced by the mentioned instrument 6 (see FIG. 7). The instrument 6 will then enter the central hole of the cotyloid drill 11 and the carrying arm 4 is unscrewed to permit the rotation of said drill driven by the motor 13 (see FIG. 8).

Figure 8:
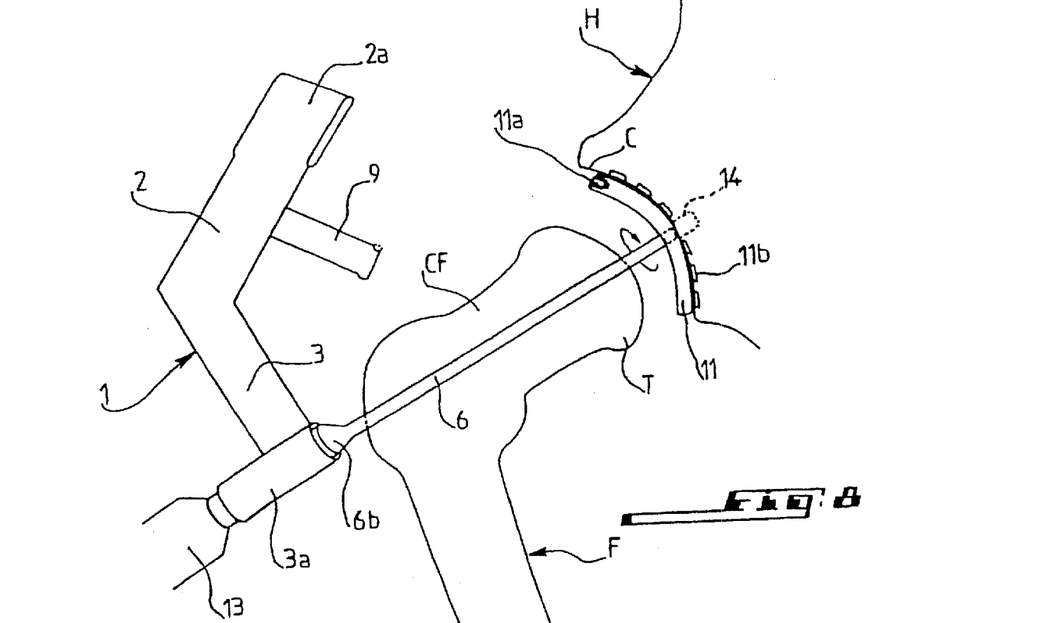

The drilling operations are now concluded and the drill 11 is withdrawn in the same manner by a pliers (not shown) introduced through small route provided during arthrotomy.

Figure 9:
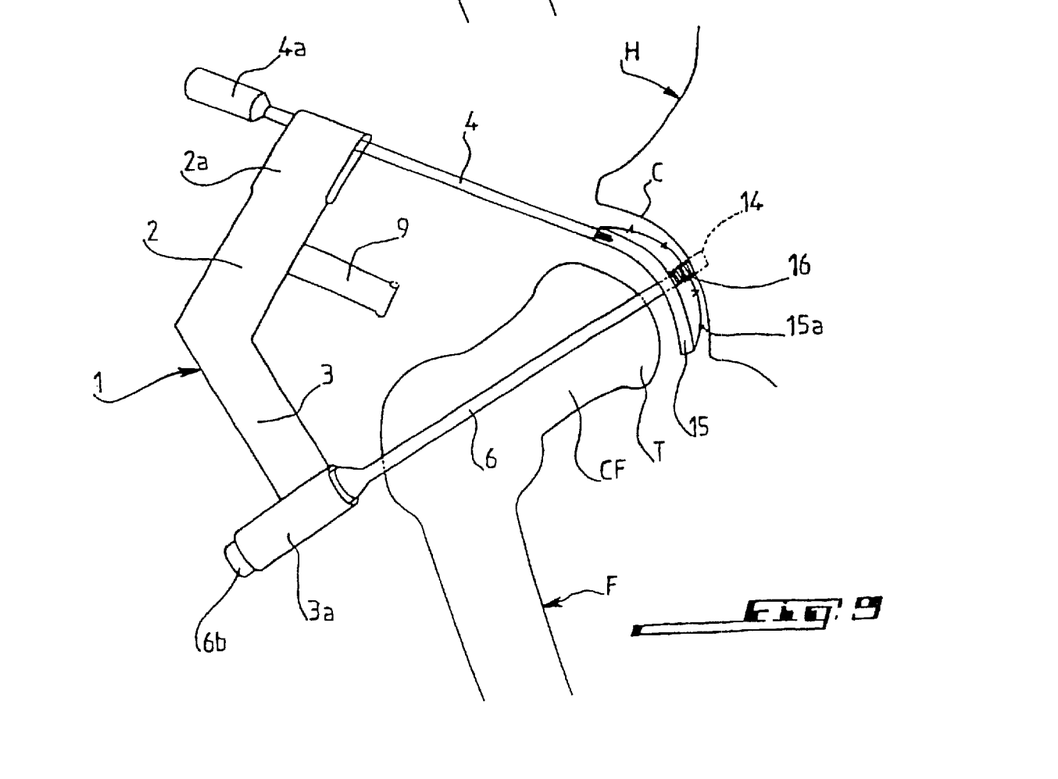
FIGS. 9 and 10 are views similar to FIG. 1 but showing the emplacement of the cotyloid implant.

The surgeon will now introduce a cotyloid implant 15 into the articular space with the aid of the carrying arm 4 whose screw-threaded distal end is screwed into a female thread provided at the periphery of said implant.

It will be seen in FIG. 9 that a screw or screw-threaded lug 16 has first been screwed through the central-hole 15b of the cotyloid implant 15, so as to be introduced simultaneously with the implant into the articular space.

Figure 13:
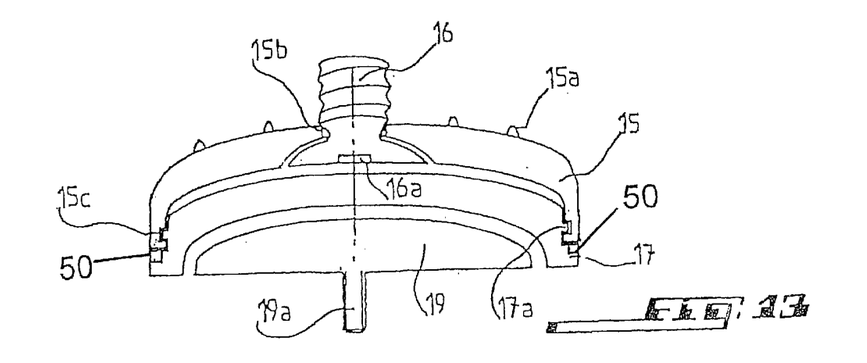
FIG. 13 is an enlarged view in axial cross-section of the cotyloid implant provided with its insert and of the impactor element.

Preferably, the head of the screw-threaded lug 16 has a peripheral rounded shape whose hollow center 16a is hexagonal, which permits positioning it over the hexagonal distal end of the same instrument 6 (see FIG. 13).

There can be provided on the handle 6b of the instrument 6 a graduated scale indicating to the operator how far he must introduce the rod 6 along the axis of the femoral neck CF for drilling of the femoral head T and then of the acetabulum C. For example, the graduation corresponding to drilling the acetabulum C will be spaced ten mm from that corresponding to drilling the femoral head T. Preferably, the central hole of the femoral drill 5 and cotyloid drill 11 and the hollow hexagonal heads 16a of the screw 16 are similarly dimensioned so as to be able to use the same instrument 6.

Once the instrument 6 is engaged in the head of the screw-threaded lug 16, this latter is screwed into the centro-cotyloid hole 14 hollowed out in the bottom of the acetabulum C. During this screwing operation, the carrying arm still supports the cotyloid implant 15, by means of its distal end 4b which is screwed into the peripheral female thread 15b of the cup.

Figure 10:
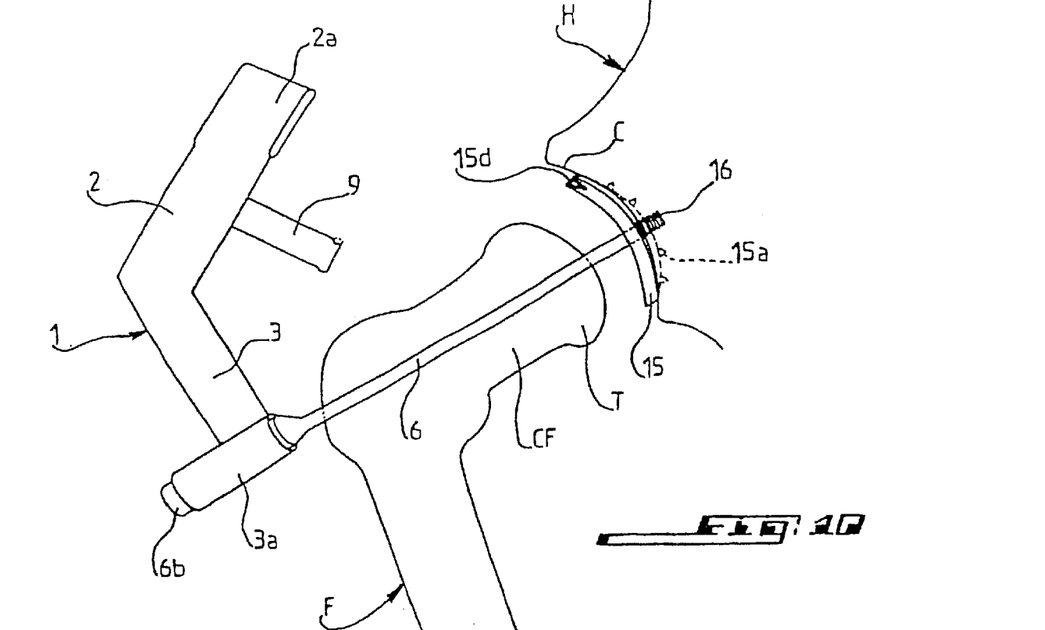

At the end of screwing, the carrying arm 4 is withdrawn and the screwing of the screw-threaded lug 16 is carried out with the instrument 6 to obtain good impaction of the cotyloid implant 15 in the acetabulum C. It will then be seen in FIG. 10 that the asperities or metallic points 15a provided on the convex surface of the implant 15 penetrate into the cotyloid bone previously drilled.

Figure 12:
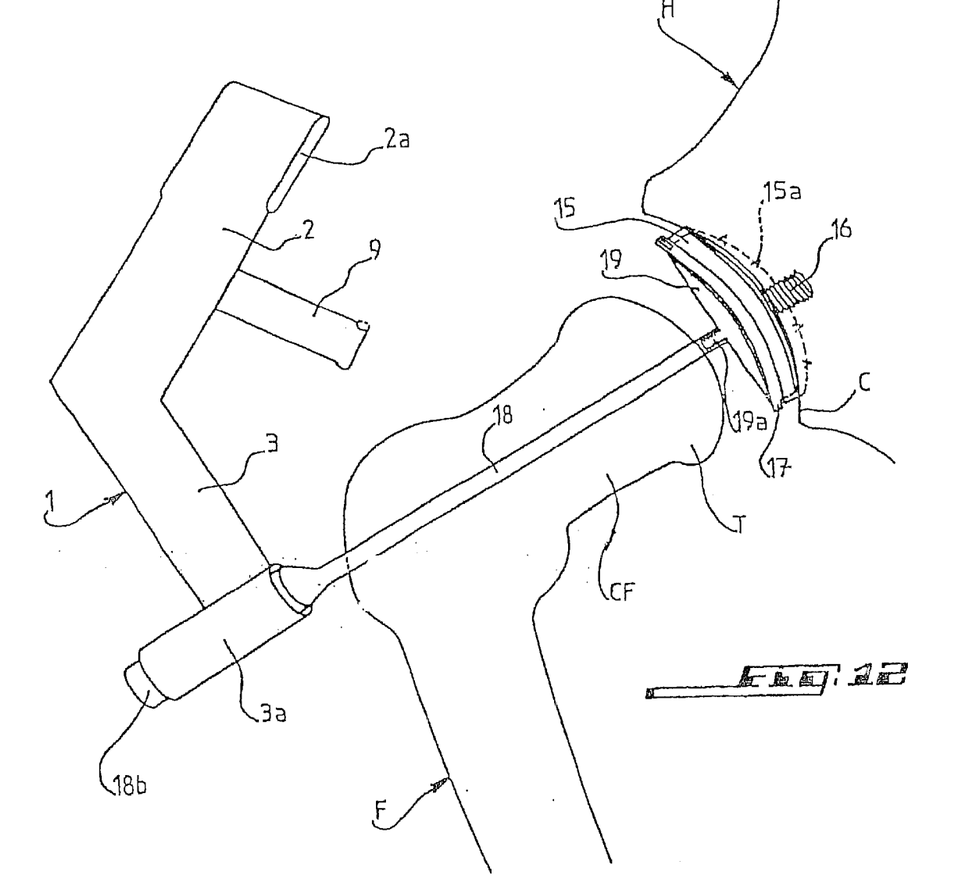

To emplace the polyethylene insert 17, there is again used the carrying arm 4 which is screwed at the periphery of this insert in a manner analogous to the drills 5 and 11 and to the implant 15, but here another instrument 18 is used in place of the instrument 6 (see FIG. 12).

Figure 11:
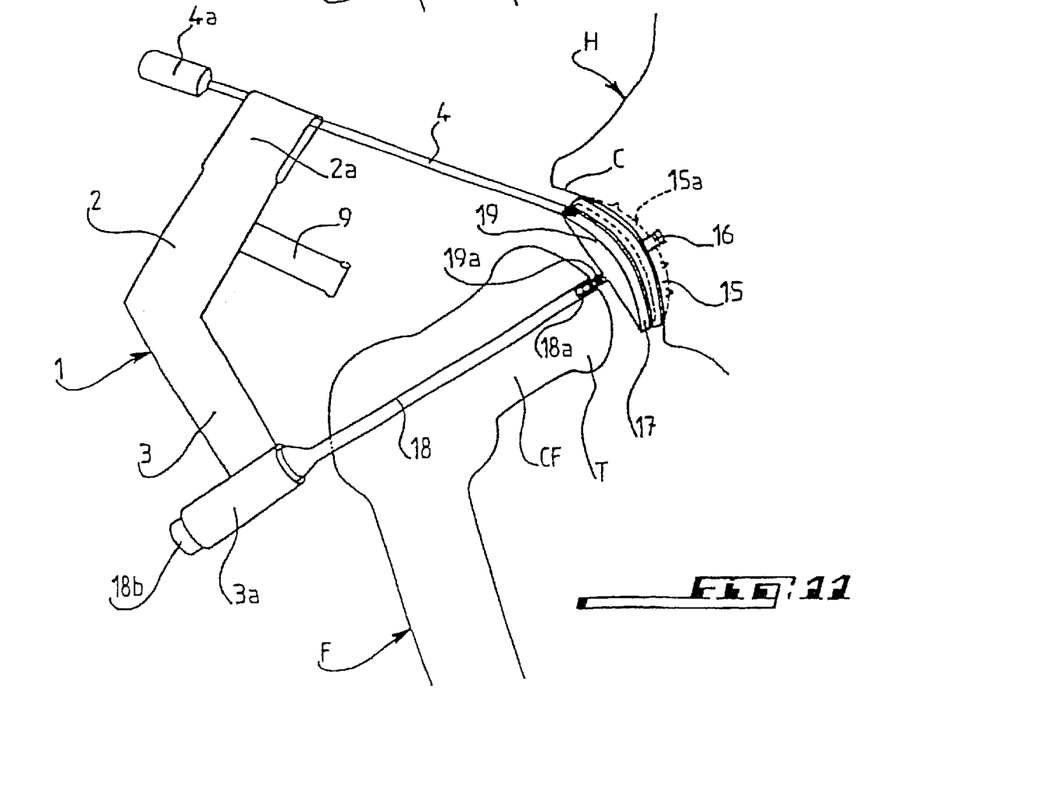
FIGS. 11 and 12 are views similar to FIG. 9, but showing the emplacement of the insert of polyethylene.

Thus, as is clearly shown in FIGS. 11 to 13, the insert or hub 17 does not engage directly on the distal end of the instrument 18, but via an impactor 19 temporarily fixed in the concave recess of the insert 17.

Although not shown, the impactor element 19 is provided by frangible peripheral points on the insert 17. The impactor element 19 is provided on its lower surface with a small central screw-threaded rod 19a which is adapted to be screwed onto the female-threaded distal end 18a of the instrument 18. This latter comprises in a manner similar to the instrument 6, a handle 18b on its proximal portion.

As is more clearly seen in FIG. 13, the insert 17 is provided at the periphery of its external convex surface with several projections or lugs 17a which are adapted to enter the corresponding recesses or mortises 15c provided in the periphery of the concave internal recess of the cotyloid implant 15. The assembly of the lugs 17a and the recesses 15c forms a connection means of the mortise-tenon type to assemble stably and rigidly the insert 17 in the cotyloid implant 15.

As is seen in FIG. 11, the distal end 18a of the instrument 18 is first screwed onto the screw-threaded rod 19a of the impactor element 19. The carrying arm 4 is withdrawn once the instrument 18 is fully screwed onto the rod (see FIG. 12). There is then exerted an axial pressure by striking the proximal end of the sleeve 18b to impact the insert 17 into the corresponding recess of the cotyloid prosthesis 15.

There can be provided a metallic circle or ring (not shown) embedded in the insert 17 at the level of one of its parallels to eventually control, for example with an amplifier of brilliance, whether the impaction of the insert into the cup is correct. For example, if the metallic ring is exactly superposed with the peripheral edge of the metallic cup, this signifies that the impaction is correct.

The impactor element 19 is then disengaged from the insert 17, by exerting a simple pull on the instrument 18 till the frangible points break. The frangible points having a resistance to traction that is less than that of the mortisetenon assembly between the insert 17 and the cup 15, the impactor 19 will be detached without risking loosening the insert from the cup. Instead of exerting a pull, one could also use the rotation of the instrument 18 in the direction of its screwing on the screw-threaded rod 19a, to give rise to rupture of the frangible points by shearing.

Finally, when the impactor 19 is freed, this latter is withdrawn with the help of a pliers introduced through the small lateral access root, after having unscrewed the instrument 18.

There could be provided as a modification, in place of the screw-threaded rod 19a, a hexagonal hole corresponding to the hexagonal head of the distal end 6a of the instrument 6 to obtain the same result. Thus, the impaction of the insert in the cup will take place in an analogous manner and the impactor 19 will be loosened from the insert by exerting a rotative couple on instrument 18.

This modification has the advantage of using the same instrument 6 for implantation also of the insert 17.

Of course, the resistance to shearing of the frangible points between the impactor 19 and the insert 17 will be determined such as to be less than that of the anchoring points 15a of the cup 15 in the acetabulum C.

For example, the frangible points could be three in number and constituted by small polyethylene welds.

Reference will now be had to FIGS. 14 to 18 for the implantation of the femoral implant 20. The femoral implant 20 here has the general shape of a spherical cap whose external convex surface is smooth to be articulated in a sliding manner within the concave recess of the insert 17, and whose internal concave surface is provided with asperities or small points 20b which are adapted to anchor on the femoral head T previously drilled. The femoral implant 20 comprises also at the center of its concave surface a small screw-threaded rod 20a analogous to the rod 19a described above and a peripheral female thread 20c (see FIG. 16) for its connection with the carrying arm 4.

Of course, the female thread could be replaced by another equivalent means permitting the connection of the implants or the drills with the carrying arm 4.

Figure 14:
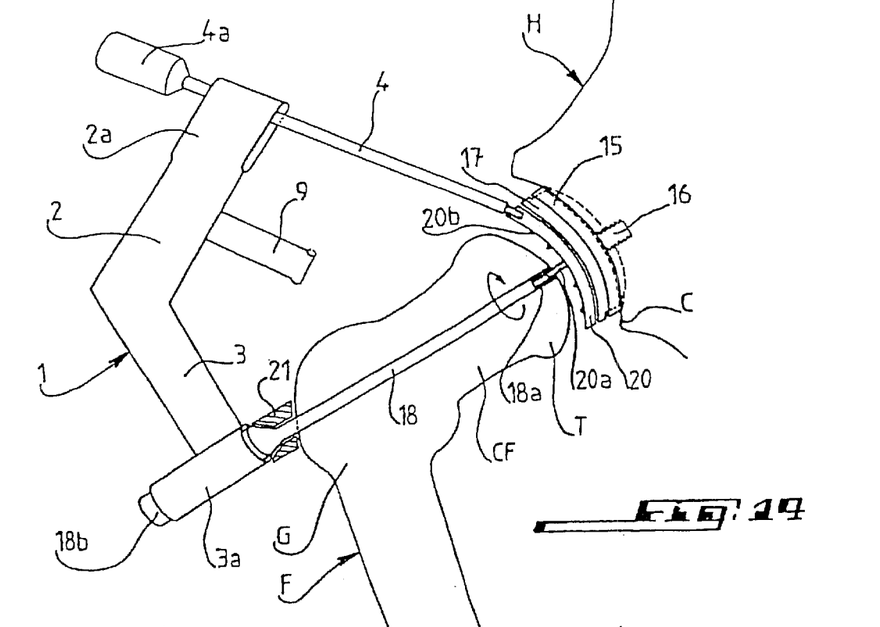
FIGS. 14 to 16 are similar to FIG. 9, but show the successive steps of the emplacement of the femoral implant.

It will be seen in FIG. 14 that the distal end 18a of the instrument 18 is screw-threaded on the small screw-threaded rod 20a of the femoral implant 20 which is carried at its periphery by the carrying arm 4.

For implantation of the femoral implant 20, the instrument 18 is used conjointly with a sleeve forming an abutment 21 into which is introduced the rod of the instrument 18 so as to be interposed between the trochanter base G and the sleeve 18b of the instrument 18.

The abutment sleeve 21 is dimensioned such that the distal end 18a of the instrument 18 will not clear the surface of the femoral head, which permits impacting the femoral implant 20 on the femoral head T by screwing to the bottom the instrument 18 on the screw-threaded rod 20a.

Figure 15:
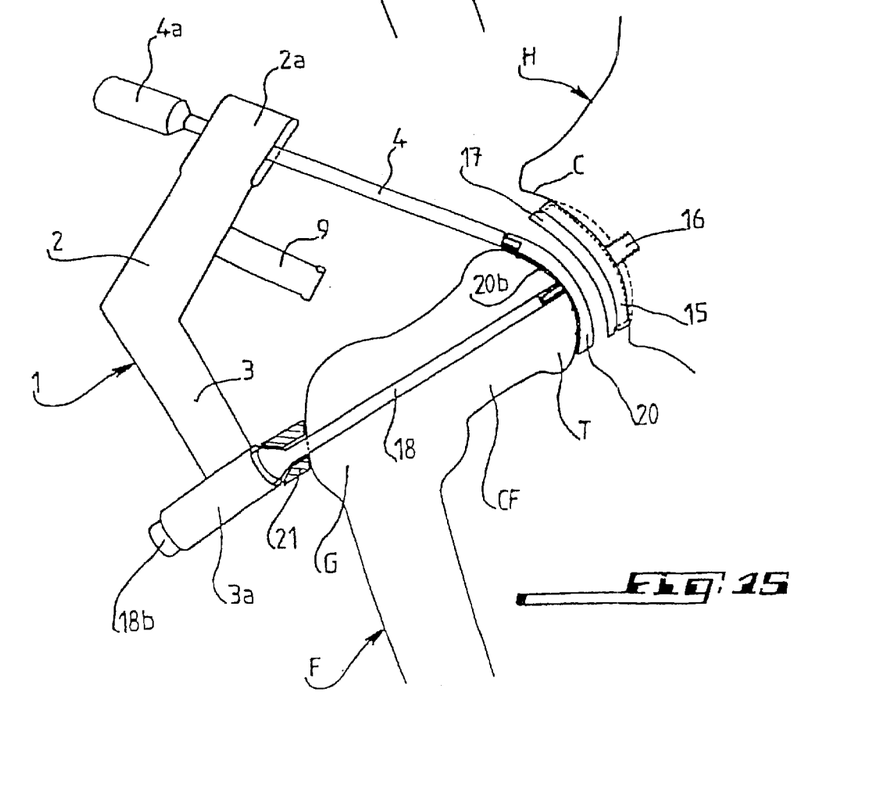
Figure 18:
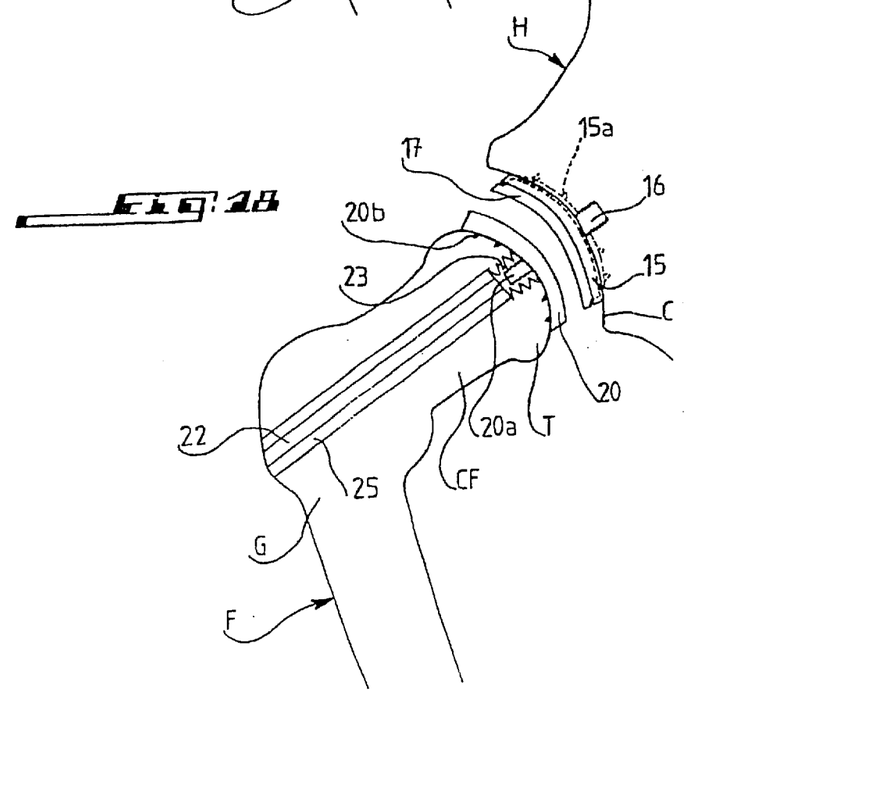
FIG. 18 shows the total hip prosthesis of the invention, implanted in the hip.

There is thus obtained, as seen in FIG. 15, an anchoring of the femoral implant 20 on the drilled head of the femoral head T with the screw-threaded rod 20a inserted into the channel 22 passing through the femoral neck CF along its axis (FIG. 18).

The screw-threaded rod 20a ensures centering of the femoral implant 20 on the femoral head T, but does not contribute to its primary anchoring, because its external diameter is less than that of the rod 18 and hence of the channel 22 which has been provided along the axis of the femoral neck CF (see FIG. 18).

Although this screw-threaded rod 20a can take place in the secondary anchoring during osseous remodeling, it is preferable to use another separate element 23 to remain fixedly in place the rod 20a on the femoral head T.

This element 23 has the shape of a nut whose internal screw-threading corresponds to that of the rod 20a and which comprises on its peripheral external surface another screw-thread whose thread bottom has a cross-section corresponding to that of the mentioned channel 22.

The element 23 is introduced through the channel 22 from the trochanter region G with the help of another instrument 24 which supports at its distal end 24a the nut 23. The distal end 24a of the instrument 24 comprises for example three lugs to secure in rotation the nut 23 to the instrument 24. Thus, with the help of the instrument 24, the nut 23 is screwed into the channel 22, as indicated by screw-treading 25 in FIG. 18, and becomes threaded onto the rod 20a at the end of its movement.

The nut 23 is screwed to the bottom on the screw-threaded rod 20a to come into abutment against the concave surface of the implant 20. The instrument 24 is then easily withdrawn because it is secured to the nut 23 only in rotation by simple contact.

Given that the bottom of the external screw-thread of the nut 23 has a cross-sectional diameter equal to or less than that of the channel 22, the introduction of this element 23 will not enlarge the principal cross-section of the channel 22. Moreover, by providing an external screw-thread on the nut 23 with a pitch which is more spaced and wider, the density of osseous spongy tissue will be substantially pre-served, which avoids rendering fragile the femoral neck CF.

Figures 16, 17:
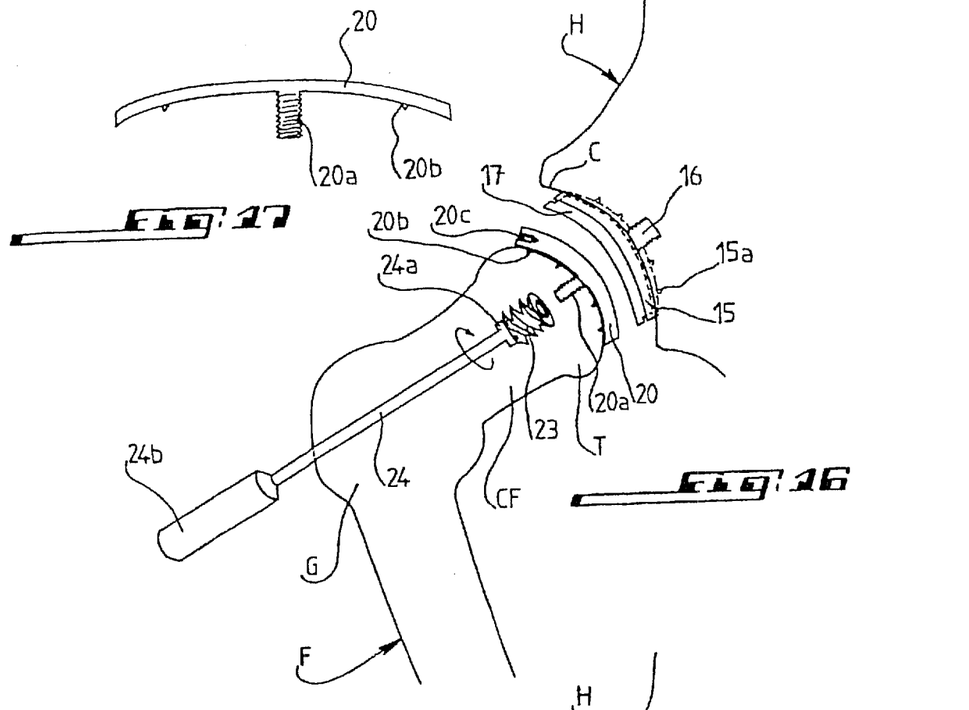
FIG. 17 is an enlarged view in axial cross-section, of the cap of the femoral implant of FIG. 16.

The instrument 24 can be held by the support structure 1 at the level of its proximal handle 24b, or else it can be used alone, as shown in FIG. 16.

Of course, the relative position between the femoral head T and the acetabulum C has been shown on the drawings in a manner which does not completely reproduce the anatomical parameters, for purposes of clarity and simplification. Similarly, the overall shape of the cup 15 and of the femoral implant 20 will not necessarily be spherical, but will be dimensioned so as to reproduce the anatomical data, so as to ensure good cotyloidal covering of the femoral head.

It will be noted particularly that the invention preserves the osseous structure and the surrounding articular capsule.

Although the invention has been described in connection with a particular embodiment, it is of course evident that it is not thereby limited and that it comprises all the technical equivalents of the means described as well as their combinations if the latter enter into the scope of the claims which follow.

What is claimed is:

1. Method for endo-articular implantation of a total hip prosthesis, comprising at least the steps of:
    providing a lateral access route in a coxo-femoral articular space by a small arthrotomy;
    introducing from a trochanter base region and along an axis of a femoral neck, a guide which opens at a level of said articular space, and hollowing out along said axis a cylindrical longitudinal space for receiving at least one instrument;
    resecting a cartilaginous surface of the head of the femur, without ablation of the femoral head, by introducing an instrument from the trochanter base region and along the axis of the femoral neck, the instrument introducing a femoral drill through said small lateral access route in said articular space and rotating said instrument connected to said femoral drill for completing said resection of the cartilaginous surface;
    resecting a cotyloid cavity, comprising introducing a cotyloid drill through said small lateral access route in said articular space, connecting said cotyloid drill to an instrument introduced along the axis of the femoral neck and rotating said instrument for completing the resection of the cotyloid cavity;
    implanting a cotyloid implant comprising a metallic cup in the drilled cotyloid cavity by introducing said cotyloid implant through said small lateral access route in said articular space, impacting said cotyloid implant into said cotyloid cavity by means of an instrument introduced along said femoral neck axis;
    implanting a femoral implant comprising a cap on spongy bone of the femoral head by introducing said femoral implant into said articular space through said small lateral access route, connecting said cap to an instrument introduced along the femoral neck axis and anchoring said femoral implant on the drilled femoral head.

2. The method according to claim 1, wherein said small arthrotomy is about 4 cm wide.

3. The method of claim 2, further comprising a step performed prior to providing the lateral access route of placing a patient to be operated on, in dorsal decubitus on an orthopedic table with traction and abduction of the lower limb to be operated on, without dislocating the coxo-femoral articulation in the course of the operation.

4. Method according to claim 1, wherein said step of resecting the cotyloid cavity comprises introducing a bit along said femoral neck axis, until said bit passes through a center hole pierced through said cotyloid drill, and hollowing a centro-cotyloid hole in a bottom of an acetabulum.

5. The method of claim 4, wherein said step of implanting a cotyloid implant first comprises screwing a screw or screw threaded lug through a central hole of said cotyloid implant, so as to be introduced simultaneously with said cotyloid implant into the articular space, engaging said instrument with the head of said screw for engaging said screw into the centro-cotyloid hole, until impaction of said cotyloid implant is obtained in the acetabulum.

6. Method according to claim 1, further comprising a step of emplacement of an insert forming an intermediate implant by introducing said insert through said small lateral access route in said articular space.

7. The method of claim 6, wherein the insert emplacement step further comprises impacting the insert into a corresponding concave recess of said cotyloid implant by means of an instrument introduced along said femoral neck axis.

8. Method according to claim 7, wherein the step of emplacement of an insert forming an intermediate implant further comprises introducing said insert together with an impactor temporarily fixed thereto in a concave recess of said insert, connecting said impactor in said articular space to said instrument, impacting said insert by exerting an axial pressure on said instrument, and disengaging the impactor from the insert.

9. The method of claim 8, wherein the impactor is initially connected to the insert by frangible points, and wherein the impactor is disengaged from the insert by exerting a force on said instrument to break the frangible points.

* * * * *